United States Patent [19]

Fehr et al.

[11] Patent Number: 4,868,340
[45] Date of Patent: Sep. 19, 1989

[54] PROCESS FOR THE PREPARATION OF CYCLOALIPHATIC ALDEHYDES

[75] Inventors: Charles Fehr, Versoix; José Galindo, Geneva, both of, Switzerland

[73] Assignee: Firmenich S.A., Geneva, Switzerland

[21] Appl. No.: 91,639

[22] Filed: Sep. 1, 1987

[30] Foreign Application Priority Data

Sep. 25, 1986 [CH] Switzerland ............ 3847/86

[51] Int. Cl.$^4$ ............................................. C07C 45/42
[52] U.S. Cl. ..................................... 568/447; 568/446
[58] Field of Search ...................... 568/447, 420, 446

[56] References Cited

U.S. PATENT DOCUMENTS 4,026,824 5/1977 Pittet .................................. 568/447

OTHER PUBLICATIONS

Arctander, S., Perfume and Flavor Chemicals (Aroma Chemicals), I, Arctander-Montclair, N.J., 1969, 760.

Primary Examiner—Werren B. Lone
Attorney, Agent, or Firm—Pennie & Edmonds

[57] ABSTRACT

Process for the preparation of cycloaliphatic aldehydes of formula

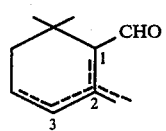

(I)

having either an isolated double bond in position 1 or 2 (endocyclic or exocyclic), or two conjugated double bonds in position 1 and 3 or 2(exocyclic) and 3 of the ring as indicated by the dotted lines, which process consists in subjecting to a deprotonation an ester of formula

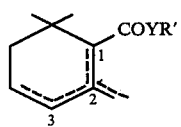

(II)

wherein the dotted lines have the above given meaning and Y designates an oxygen atom or a sulphur atom and R' stands for a linear or branched alkyl radical or a substituted or unsubstituted phenyl group, followed by H$^\ominus$ addition and hydrolysis.

8 Claims, No Drawings

PROCESS FOR THE PREPARATION OF CYCLOALIPHATIC ALDEHYDES

BRIEF SUMMARY OF THE INVENTION

The present invention relates to a process for the preparation of cycloaliphatic aldehydes of formula

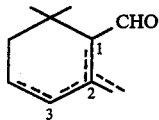
(I)

having either an isolated double bond in position 1 or 2 (endocyclic or exocyclic), or two conjugated double bonds in position 1 and 3 or 2(exocyclic) and 3 of the ring as indicated by the dotted lines, which comprises the following subsequent reaction steps:

a. deprotonation of an ester of formula

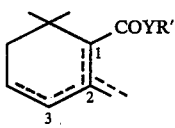
(II)

wherein the dotted lines have the above given meaning, symbol Y designates an oxygen or sulphur atom and R' represents a linear or branched alkyl radical, preferably a $C_1$ to $C_6$ radical, or a substituted or unsubstituted phenyl;

b. addition to the thus formed enolate or formula

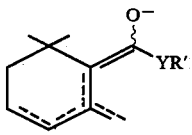
(III)

of a reducing agent capable to generate $H^\ominus$ anions in the reaction conditions, followed optionally by the treatment of the obtained product with a trialkylsilyl halide; and c. hydrolysis of the resulting product.

BACKGROUND OF THE INVENTION

The present invention relates to the area of organic synthesis and in particular it relates to a process for the preparation of cycloaliphatic aldehydes starting from the corresponding alkyl esters.

Due to the importance of aldehydic compounds in various chapters of organic synthesis, either as intermediates or as useful end-products, namely for the preparation of perfurmery and aroma chemicals, this type of process possesses a great industrial importance. Suffice it to mention the role of certain unsaturated cycloaliphatic aldehydes such as alpha- or beta-cyclocitral or of beta-safranal. These compounds are generally obtained by complex processes, hence the interest to dispose of novel methods, which are both simple and industrially economical to implement.

The present invention offers precisely an original solution to the problem presented by their synthesis.

THE INVENTION

The instant invention relates to a process for the preparation of cycloaliphatic aldehydes of formula

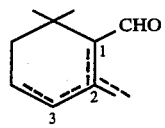
(I)

having either an isolated double bond in position 1 or 2 (endocyclic or exocyclic), or two conjugated double bonds in position 1 and 3 or 2(exocyclic) and 3 of the ring as indicated by the dotted lines, which comprises the following subsequent reaction steps:

a. deprotonation of an ester of formula

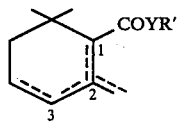
(II)

wherein the dotted lines have the above given meaning, symbol Y designates an oxygen or sulphur atom and R' represents a linear or branched alkyl radical, preferably a $C_1$ to $C_6$ radical, or a substituted or unsubstituted phenyl;

b. addition to the thus formed enolate or formula

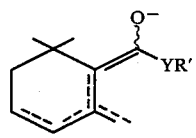
(III)

of a reducing agent capable to generate $H^\ominus$ anions in the reaction conditions, followed optionally by the treatment of the obtained product with a trialkylsily halide; and c. hydrolysis of the resulting product.

The above described process can be represented by the following reaction scheme.

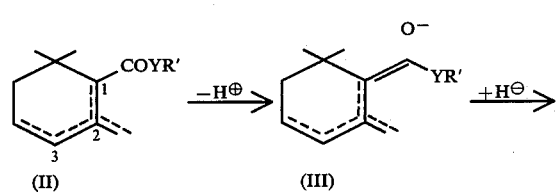

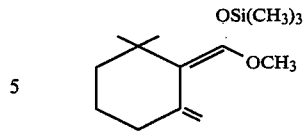

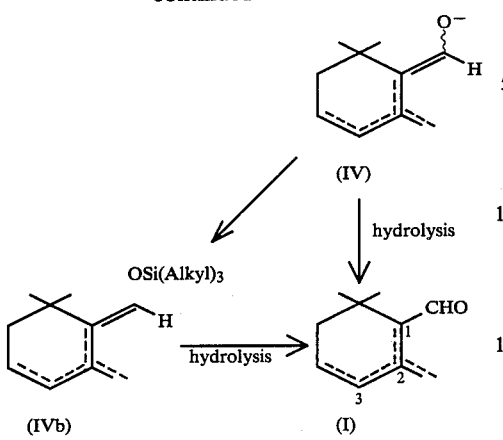

by adding trimethyl-silylchloride to the reaction mixture, after treating methyl gamma- or beta-cyclogeranate with a strong base according to the invention. This fact suggests that the transient-intermediate is very probably present under the form of an enolate such as that indicated by formula (IIIc), which compound could originate either from the direct deprotonation of ester (II) or from the action of the strong base utilized (or of a nucleophile) on the ketene-acetal of formula (IIIb) according to the following scheme:

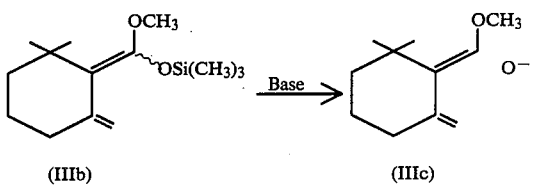

Suitable starting material of formula (II) includes cycloaliphatic esters chosen among the lower alkyl esters of alpha-, beta- or gamma-cyclogeranic acids or of beta- or gamma-safranic acid. Among the preferred esters, one can mention methyl or ethyl alpha-, beta- and gamma-cyclogeranate as well as their higher homologs n-propyl, iso-propyl and butyl, or methyl or ethyl beta- and gamma-safranate. These products are commercially available or can be readily synthesized according to known methods. As starting materials one can also use thioesters. Preferred thioesters include S-phenyl alpha- or beta-thiocyclogeranate.

The first step of the process, which consists in the deprotonation of the said starting esters, is promoted by the action of a strong base. Suitable strong base include alkali metal alkyl derivatives such as propyl- or butyl-lithium, or alkali metal amide, preferably lithium amides.

Thus, bases such as lithium dimethyl-, diethyl- or diisopropyl amide constitute preferred bases.

Other strong bases such as lithium dicyclohexyl amide or bases such as those represented by the formulae

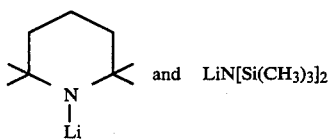

can also be employed.

Mixtures consisting of two of the said bases can also be used.

The reaction is carried out in inert organic solvents, for example by dissolving the starting ester in an ether such as tetrahydrofuran, and the base in an aliphatic, cycloaliphatic or aromatic hydrocarbon, for example in hexane, cyclohexene, benzene or toluene.

Without precluding the correctness of the mechanistic interpretation of the reaction which characterizes the first step of the process, we can assert that the product formed occurs in the form of a transient intermediate in the chosen reaction conditions. Indirect evidence tends to confirm however its structure. It has been possible in fact to isolate a silyl derivative of formula With regard to the reaction temperature of this first step of the invention process, we have observed that its value can be of about the room temperature or slightly lower than the room temperature, for example at about 15°–25° C. According to a preferred embodiment, by using n-butyl-lithium as a base and methyl-beta-cyclogeranate as a starting ester, the reaction can be effected at about 15° C.

Lower temperatures can also be used. For example, by treating S-phenyl 2,6,6-trimethyl-1-cyclohex-1-en-1-carbothioate with n-butyl-lithium, the reaction can be easily carried out at −78° C.

Suitable reducing agents, which could generate $H^{\ominus}$ anions in the reaction conditions, include metal hydrides, for example alkali metal hydride or aluminum or boron hydride complexes such as sodium bis(2-methoxyethoxy)aluminum hydride (VITRIDE), sodium diethyldihydroaluminate (OMH-1), diisobutylaluminum hydride (DIBAH), lithium aluminum hydride (LiAlH$_4$), lithium-triisobutyl borohydride, lithium-triisoamyl borohydride or other analogous complexes known under the names of SELECTRIDES (registered tradename of Aldrich Co.). Preferred reducing agents include those complexes having the following generic formula $$M^1M^2X_{4-n}H_n$$

wherein $M^1$ designates a boron or an aluminum atom, $M^2$ an alkali metal atom, preferably sodium or lithium, and index n represents an integer having a value of 1, 2 or 3.

The last step of the invention process is carried out by hydrolyzing the obtained product by treating it with water, preferably in a slightly acidic medium, for example by means of an icy aqueous solution of ammonium chloride. Hydrolysis can also be effected by means of a hydroxylated derivative, for example by means of an aliphatic alcohol. 2-Butanol is preferably used to this effect.

As indicated above, the hydrolysis which characterizes step c. of the process of the invention can be carried out directly on product (IV), resulting from the addition of the reducing agent to enolate (III). Alternatively, it is possible to convert the resulting product into a silyl ether of formula

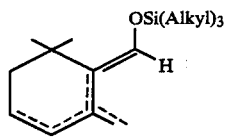

by adding to resulting product (IV) trialkyl-silyl chloride and hydrolyzing ether (IVb) to give the desired aldehydes. The resulting aldehydes however occur in the form of an isomeric mixture the composition of which is slightly different from that of the product resulting from the "direct" hydrolysis. For example, by subjecting methyl beta-safranate to the process of the invention with butyl-lithium, followed by reduction and hydrolysis with a concentrated aqueous solution of ammonium chloride, safranal is obtained as a gamma-/beta-mixture, the isomeric content of which is 55/45 respectively. On the other hand, by preliminarily converting product (IVb) into its silanyl ether derivative, the hydrolysis of this latter compound gives beta-safranal in a purity of about 95%.

The usual treatments of phase separation, neutralization and distillation enable to obtain the desired products.

The invention is illustrated in a more detailed manner by the following examples wherein the temperatures are indicated in degrees centrigrade and the abbreviations have the meaning current in the art.

EXAMPLE 1

Preparation of alpha-cyclocitral 9.3 Ml of a 1.42N slution of butyl-lithium in hexane (0.0132M) were added dropwise at −78° to a solution of 2.0 g (0.011M) of methyl alpha-cyclogeranate in 40 ml of anhydrous tetrahydrofuran (THF). Once the addition was over, the temperature of the mixture was increased to +15° and, at this temperature, 3.17 ml (0.011M) of a 70% solution of VITRIDE [sodium bis(2-methoxyethoxy)aluminum hydride] in toluene were added thereto. The reaction mixture was heated to 40° for 45 mn, then hydrolyzed by pouring it onto an icy saturated aqueous solution of ammonium chloride. The mixture was extracted with ether, the organic phase was separated and then subjected to the usual treatments of neutralization and washing to give a residue which, upon distillation, gave 1.27 g of alpha-cyclocitral having b.p. 60°–65°/66 Pa (purity: 80%; yield: 65%).

EXAMPLE 2

Preparation of beta-cyclocitral

163 Ml of a 1.42N solution of butyl-lithium (0.231M) in hexane were rapidly added at −10/+15° to a solution of methyl beta-cyclogeranate (30 g; 0.165M) in 150 ml of THF. The reaction mixture was left reacting for 5 mn at 15° and thereafter poured onto a suspension of 3.15 g (0.083M) of LiAlH₄ in 150 ml of THF. The temperature increases steadily up to 30° where it stablizes. The mixture was heated until it reached 40° and kept at this temperature during 2 hours, thereupon it was cooled at about −15° and 44.85 g of trimethyl-silyl chloride (0.413M) were added. The temperature was increased to room temperature and the mixture was then hydrolyzed under a nitrogen atmosphere by pouring it onto an icy saturated aqueous solution of ammonium chloride. The mixture was then extracted with ether and the combined organic extracts were subjected to the usual treatments of neutralization, washing and evaporation while the obtained residue was dissolved in THF. The resulting solution was hydrolyzed by treating it with 0.5 g of p-toluene sulfonic acid for 20 mn. Then, the mixture was poured onto a saturated aqueous solution of sodium bicarbonate mixed with ice and extracted with ether. The ethereal layer was then subjected to the usual treatments of drying, concentration and finally distillation to give 16.9 g of beta-cyclocitral (purity: 94%; yield: 63%).

EXAMPLE 3

Preparation of beta-cyclocitral 54.2 Ml (0.077M) of a 1.42N solution of butyl-lithium in hexane were added at −10/+15° to a solution of 10.0 g (0.055M) of methyl beta-cyclogeranate in 150 ml of anhydrous THF. After having been left at 15° during 5 mn, there were added to the reaction mixture 15.9 ml of a 70% solution of VITRIDE in toluene (0.055M). The temperature of the mixture was then raised to 40° and, at this temperature, it was left under stirring for 45 mn. The mixture was then rapidly poured at 15° onto a solution of 20.35 g (0.275M) of 2-butanol in 100 ml of THF. At the end of the reaction, 150 ml of a 5% aqueous HCl were rapidly added and an extraction was then carried out with ether. The combined organic extracts were washed, dried over Na₂SO₄ and concentrated to give a residue which, on distillation in a bulb apparatus, gave 7.74 g of beta-cyclocitral (purity: 76%; yield: 70%). By carrying out the hydrolysis with a saturated aqueous solution of ammonium chloride or with aqueous HCl instead of 2-butanol, a mixture of beta-/gamma-cyclocitral was obtained the isomeric content of which was of about 70/30.

EXAMPLE 4

Preparation of beta-cyclocitral 2.0 G (0.011M) of methyl beta-cyclogeranate were slowly added at −78° to a solution of lithium diisopropylamide (1.05 equiv.) in 30 ml of THF. Once the introduction is over, the temperature of the reaction mixture was increased to 15° and 3.17 ml (0.011M) of a 70% solution of VITRIDE in toluene were rapidly added thereto. The reaction temperature was increased to 40° and after 45 mn, the mixture was treated with 4.07 g of 2-butanol (0.055M). After subjecting the mixture to the same treatments as those described in the previous example, 1.31 g of beta-cyclocitral was obtained by distillation at 45°–50°/1.33 Pa (yield: 67%). By carrying out the hydrolysis by means of a saturated aqueous solution of ammonium chloride or by means of aqueous HCl instead of 2-butanol, a mixture of beta-/gamma-cyclocitral was obtained with an isomeric content of about 70/30 respectively. In view of the fact that alpha-cyclocitral isomerizes easily to beta-cyclocitral, this latter compound can be easily synthesized starting from a mixture of methyl alpha- and beta-cyclogeranate or simply from the alpha-isomer.

EXAMPLE 5

Preparation of beta-safranal 82.1 Ml (0.117M) of a 1.42N solution of butyl-lithium in hexane were added at −78° to a solution of 20.0 g (0.111M) of methyl beta-safranate in 200 ml of THF. At the end of the introduction, the temperature of the mixture was increased to 15° and the mixture was poured onto a suspension of 2.11 g (0.056M) of LiAlH$_4$ in 200 ml of THF. The temperature was increased to 40° and the mixture was left under stirring for about 1½ hour. By carrying out the hydrolysis at this stage by means of a saturated aqueous solution of ammonium chloride and by carrying out the following operations as indicated in the previous examples, a mixture of beta-/gamma-safranal was obtained with an isomeric content of 45/55 respectively. The mixture was cooled at −15° and 30.14 g (0.278M) of trimethylsilyl chloride were added thereto and the temperature was increased to room temperature. The following hydrolysis was carried out with a mixture of ice and 5% HCl solution. After filtration, evaporation and distillation of the residue, 14.2 g of beta-safranal were obtained at 60°–65°/66 Pa (purity: 95%; yield: 81%).

EXAMPLE 6

Preparation of beta-safranal 41.4 Ml (0.059M) of a 1.42N solution of butyl-lithium in hexane were added at −78° to a solution of 10.0 g (0.056M) of methyl beta-safranate. At the end of the introduction, the reaction temperature was increased to 15° and 16.16 ml (0.056M) of a 70% solution of VITRIDE in toluene were added thereto. The temperature of the mixture was increased to 40° and, after having been left for 45 mn under stirring, the mixture was treated with 15.2 g (0.140M) of trimethylsilyl chloride. After the usual treatments, a distillation of the obtained residue gave 7.54 g of beta-safranal at 60°–65°/66 Pa (yield: 85%).

What we claim is:

1. Process for the preparation of cycloaliphatic aldehydes of formula

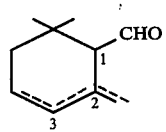

(I)

having either an isolated double bond in position 1 or 2 (endocyclic or exocyclic) or two conjugated double bonds in position 1 and 3 or 2(exocyclic) and 3 of the ring as indicated by the dotted lines, which comprises the following subsequent reaction steps:

a. deprotonation of an ester of formula

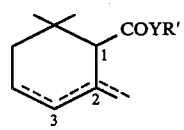

(II)

wherein the dotted lines have the above given meaning, symbol Y designates an oxygen or sulphur atom and R' represents a linear or branched alkyl radical or a phenyl radical;

b. addition to the thus formed enolate or formula

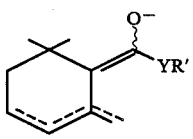

(III)

of a reducing agent capable to generate H$^\ominus$ anions in the reaction conditions, followed optionally by the treatment of the obtained product with a trialkyl-silyl halide; and c. hydrolysis of the resulting product.

2. Process according to claim 1 wherein the deprotonation is carried out by treating the ester of formula (II) with a strong base.

3. Process according to claim 2 wherein the strong base is an alkali metal alkyl derivative or an alkali metal amide.

4. Process according to claim 3 wherein the strong base is selected from the group consisting of propyl-lithium, butyl-lithium or lithium dimethyl-, lithium diethyl- and lithium diisopropyl-amide.

5. Process according to one of claims 2 to 4 wherein the base is used in an amount higher than the equivalent amount of starting ester (II).

6. Process according to claim 1 wherein the reducing agent capable to generate H$^\ominus$ anions is selected from the group consisting of an alkali metal hydride, a lithium trialkoxyaluminum hydride and sodium bis(2-methoxyethoxy)aluminum hydride.

7. Process according to claim 2 wherein the starting ester of formula (II) is methyl or ethyl alpha- or beta-cyclogeranate, or methyl or ethyl beta-safranate, the strong base is butyl-lithium or lithium diisopropylamide and the reducing agent capable to generate H$^\ominus$ anions is sodium bis(2-methoxyethoxy)aluminum hydride to give, after hydrolysis, alpha- or beta-cyclocitral and beta-safranal, respectively.

8. Process according to claim 1 wherein R$^1$ is a C$_1$ to C$_6$ alkyl radical.

* * * * *

UNITED STATES PATENT AND TRADEMARK OFFICE
CERTIFICATE OF CORRECTION

PATENT NO. : 4,868,340

DATED : September 19, 1989

INVENTOR(S) : Charles Fehr, et al.

It is certified that error appears in the above-identified patent and that said Letters Patent is hereby corrected as shown below:

At column 5, line 40: change "slution" to -- solution --.

At column 1, line 40: formula (III) should be

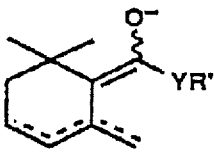

At column 2, line 45: formula (III) should be

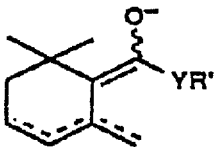

At column 2, line 65: formula (III) should be

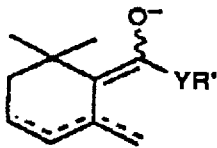

UNITED STATES PATENT AND TRADEMARK OFFICE
CERTIFICATE OF CORRECTION

PATENT NO. : 4,868,340
DATED : September 19, 1989
INVENTOR(S) : Charles Fehr, et al.

It is certified that error appears in the above-identified patent and that said Letters Patent is hereby corrected as shown below:

At column 3, line 5: formula (IV) should be

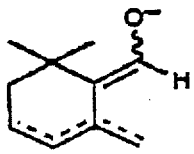

At column 3, line 15: formula (IVb) should be

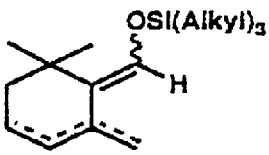

At column 4, line 5: the formula should be

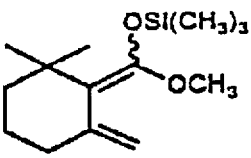

UNITED STATES PATENT AND TRADEMARK OFFICE
CERTIFICATE OF CORRECTION

PATENT NO. : 4,868,340
DATED : September 19, 1989
INVENTOR(S) : Charles Fehr, et al.

It is certified that error appears in the above-identified patent and that said Letters Patent is hereby corrected as shown below:

At column 4, line 25:   formula (IIIb) should be

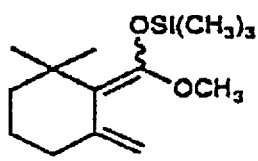

At column 4, line 25:   formula (IIIc) should be

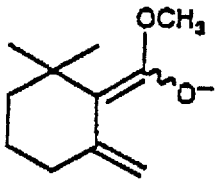

At column 5, line 10:   formula (IVb) should be

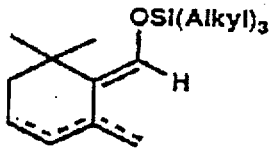

UNITED STATES PATENT AND TRADEMARK OFFICE
CERTIFICATE OF CORRECTION

PATENT NO. : 4,868,340

DATED : September 19, 1989

INVENTOR(S) : Charles Fehr, et al.

It is certified that error appears in the above-identified patent and that said Letters Patent is hereby corrected as shown below:

At claim 1, column 7, line 50: formula (I) should be

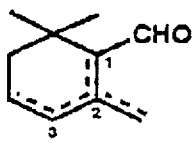

At claim 1, column 8, line 7: formula (II) should be

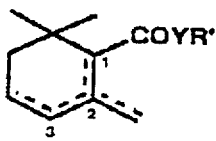

Signed and Sealed this

Second Day of October, 1990

*Attest:*

HARRY F. MANBECK, JR.

*Attesting Officer*  *Commissioner of Patents and Trademarks*